US005877166A

United States Patent [19]
Reist et al.

[11] Patent Number: 5,877,166
[45] Date of Patent: Mar. 2, 1999

[54] ENANTIOMERICALLY PURE 2-AMINOPURINE PHOSPHONATE NUCLEOTIDE ANALOGS AS ANTIVIRAL AGENTS

[75] Inventors: Elmer J. Reist, Menlo Park; Wallace W. Bradford, Redwood City; Nurulain T. Zaveri, San Jose, all of Calif.

[73] Assignee: SRI International, Menlo Park, Calif.

[21] Appl. No.: 847,881

[22] Filed: Apr. 28, 1997

Related U.S. Application Data

[63] Continuation-in-part of Ser. No. 639,614, Apr. 29, 1996.

[51] Int. Cl.$^6$ .................. A61K 31/675; C07F 9/6561
[52] U.S. Cl. .................. 514/81; 544/244; 558/159
[58] Field of Search .................. 514/8; 558/159; 544/244

[56] References Cited

U.S. PATENT DOCUMENTS

| | | | |
|---|---|---|---|
| 3,446,793 | 5/1969 | Jones et al. | 536/27 |
| 3,560,478 | 2/1971 | Myers et al. | 536/27 |
| 4,755,516 | 7/1988 | Tolman et al. | 514/262 |
| 4,808,716 | 2/1989 | Hol et al. | 544/244 |
| 4,897,479 | 1/1990 | Tolman et al. | 514/262 |
| 5,047,533 | 9/1991 | Reist et al. | 544/244 |
| 5,532,255 | 7/1996 | Reist et al. | 514/81 |

FOREIGN PATENT DOCUMENTS

| | | |
|---|---|---|
| 0452935 A1 | 10/1991 | European Pat. Off. |
| 3045375 A1 | 7/1982 | Germany. |
| 2009834 | 9/1990 | Germany. |
| 1243213 | 8/1971 | United Kingdom. |
| 1243214 | 8/1971 | United Kingdom. |
| WO 88/05438 | 7/1988 | WIPO. |
| WO 93/06112 | 4/1993 | WIPO. |
| WO 94/03466 | 2/1994 | WIPO. |

OTHER PUBLICATIONS

Duke et al., "In vitro and in vivo activities of phosphate derivatives of 9–(1,3–dihydroxy–2–propoxymethyl)–guanine against cytomegalovirus," *Antiviral Research* 6:299–308 (1986).

Engel, "Phosphonates as analogues of natural phosphates," *Chem Reviews* 77(3):349–367 (1977).

Hampton et al., "Synthesis of homoadenosine– 6'–phosphonic acid and studies of its substrate and inhibitor properties with adenosine menophosphate utilizing enzymes," *Biochemistry* 12(9):1730–1736 (1973).

Huffman et al., "Structure–activity relationship of phosphonic acid analogs of acyclovir or ganciclovir against human cytomegalovirus in MRC–5 Cells," *Nucleosides & Nucleotides* 13(1–3):607–613 (1994).

Jones et al., "The Synthesis of 6'deoxyhomonucleoside–6'–phosphonic acids," *J. Am. Chem. Soc.* 90(19):5537–5538 (1968).

Montgomery et al., "Phosphonate analogue of 2'–deoxy–5–fluorouridylic acid," *J. Med. Chem.* 22(1):109–111 (1979).

Prisbe et al., "Synthesis and antiherpes virus activity of phosphate and phoshonate derivatives of 9–[(1,3–dihydroxy–2–propoxy)methyl]guanine," *J. Med. Chem* 29:671–675 (1986).

Reist et al., "Synthesis of acyclonucleoside phosphonates as antiviral agents against cytomegalovirus," *Nucleosides & Nucleotides* 13(1–3):539–550 (1994).

Smee et al., "Antiviral activities of nucleosides and nucleotides against wild–type and drug–resistant strains of murine cytomegalovirus," *Antiviral Research* 26:1–9 (1995).

Tolman et al., Chapte 3 in ACS Symposium Series 401 John C. Martin Editor., 1989., ACS Washington DC.

*Primary Examiner*—Mukund J. Shah
*Assistant Examiner*—Pavanaram K Sripada
*Attorney, Agent, or Firm*—Dianne E. Reed; Bozicevic & Reed LLP

[57] ABSTRACT

Cyclic and acyclic 2-aminopurine phosphonate nucleotide analogs useful to treat herpes viral infections are provided in enantiomerically pure form. Pharmaceutical compositions and methods for treating herpes viral infections are provided as well, as is a chiral synthesis for preparing the novel compounds in enantiomerically pure form.

24 Claims, No Drawings

ENANTIOMERICALLY PURE 2-AMINOPURINE PHOSPHONATE NUCLEOTIDE ANALOGS AS ANTIVIRAL AGENTS

CROSS-REFERENCE TO RELATED APPLICATION

This is a continuation-in-part of U.S. patent application Ser. No. 08/1639,614, filed Apr. 29, 1996.

TECHNICAL FIELD

This invention relates generally to the field of antiviral agents, and more particularly relates to enantiomerically pure cyclic and acyclic 2-aminopurine phosphonate nucleotide analogs useful as antiviral agents. The invention additionally relates to pharmaceutical compositions containing one or more of these compounds, and to a novel chiral synthesis for preparing the compounds in enantiomerically pure form.

BACKGROUND

There are eight known herpes-type viruses which affect human beings: herpes zoster (chicken pox); herpes simplex virus I & II (cold sores and genital herpes); cytomegalovirus (cytomegalic inclusion disease); Epstein-Barr virus (mononucleosis); human β-lymphotropic virus (also known as human herpes virus VI); human herpes virus VII; and Kaposi's sarcoma herpes virus (KSHV). The herpes viruses are medium-sized viruses containing double-stranded DNA, with a nucleocapsid about 100 nm in diameter surrounded by a lipid-containing envelope. The virion is 150–200 nm in diameter and permits latent infections which last for the life span of the host even when antibodies are present.

Purine-based analogs to treat herpes infections are known and have been described, for example, in U.S. Pat. Nos. 4,808,716 to Holy et al. and U.S. Pat. No. 4,755,516 and 4,897,479 to Tolman et al. The Holy et al. patent relates to 9-(phosphonylmethoxyalkyl)adenines and their use in treating herpes simplex virus, types I & II, while the Tolman et al. disclosures describe a family of 6-substituted purines which are stated to be useful against herpes viruses in general. U.S. Pat Nos. 5,047,533 and 5,532,225 to Reist et al., each of common assignment herewith, also describe purine analogs which have antiviral activity against the Herpes group of viruses.

Phosphonate analogs of nucleotides are also described in R. Engel, *Chem. Reviews* 77(3):349–367 (1977). Phosphonate compounds which are direct cyclic nucleotide analogs are described in: U.S. Pat. No. 3,446,793 to Jones et al.; U.S. Pat. No. 3,560,478 to Myers et al.; German Patent Publications 2,009,834 and 3,045,375; British Patent Nos. 1,243,213 and 1,243,214; A. Hampton et al., *Biochemistry* 12:1730–1736 (1973); G. H. Jones et al., *J. Am. Chem. Soc.* 90:5337–5338 (1968); and J. A. Montgomery et al., *J. Med. Chem.* 22:109–111 (1979).

Other references of interest include EPO Publication No. 173,624, which discloses 9 (3-phosphono-1-propoxymethyl) guanine as an anti-herpes agent, and A. E. Duke et al., *Antiviral Res.* 6:299–308 (1986) and E. J. Prisbe et al., *J. Med. Chem.* 29:671–675 (1986), both of which relate to 9 (3-phosphono-1-hydroxymethyl-1-propoxymethyl) guanine.

The present invention now provides a novel class of antiviral nucleotide analogs. The compounds are enantiomerically pure 2-aminopurine phosphonate analogs. Surprisingly, it has been found that at least one of the isolated enantiomers, the "R" enantiomer, has significant activity against several herpes viruses while displaying no detectable kidney toxicity. Accordingly, the invention also relates to the use of the compounds to treat herpes viral infections. Further, the invention encompasses a method for synthesizing the compounds in enantiomerically pure form.

SUMMARY OF THE INVENTION

It is accordingly a primary object of the invention to provide antiviral agents useful to treat herpes viral infections.

It is another object of the invention to provide such antiviral agents in the form of enantiomerically pure 2-aminopurine phosphonate nucleotide analogs.

It is an additional object of the invention to provide a method for treating herpes viral infections using an antiviral agent as disclosed herein.

It is a further object of the invention to provide a pharmaceutical composition containing an antiviral agent of the invention in combination with a pharmaceutically acceptable carrier.

Yet another object of the invention is to provide a chiral synthesis for preparing the novel antiviral agents in enantiomerically pure form.

Additional objects, advantages and novel features of the invention will be set forth in part in the description which follows, and in part will become apparent to those skilled in the art upon examination of the following, or may be learned by practice of the invention.

In one aspect, then, the invention relates to enantiomerically pure antiviral agents represented by structural formula (A)

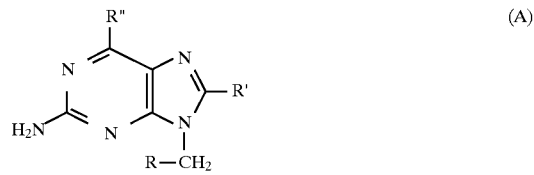

wherein:
R is selected from the group consisting of

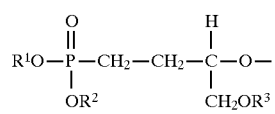

and

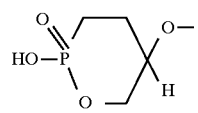

in which $R^1$ and $R^2$ are independently selected from the group consisting of hydrogen and lower alkyl, $R^3$ is lower alkyl or —$(CH_2)_n$—$C_6H_5$, and n is an integer in the range of 0 to 6 inclusive;

R' is selected from the group consisting of hydrogen, hydroxyl, carboxyl, alkoxy, amino and halogen; and R" is hydrogen or a halogen substituent, or a pharmaceutically acceptable salt or ester thereof.

Because the compounds are in enantiomerically pure form, the R substituent will in actuality be one of the following four groups:

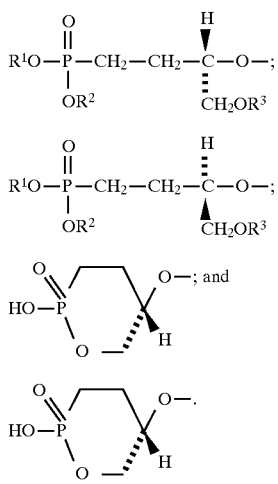

The preferred compounds herein include those represented by formulae (I), (IV), (V) and (VI)

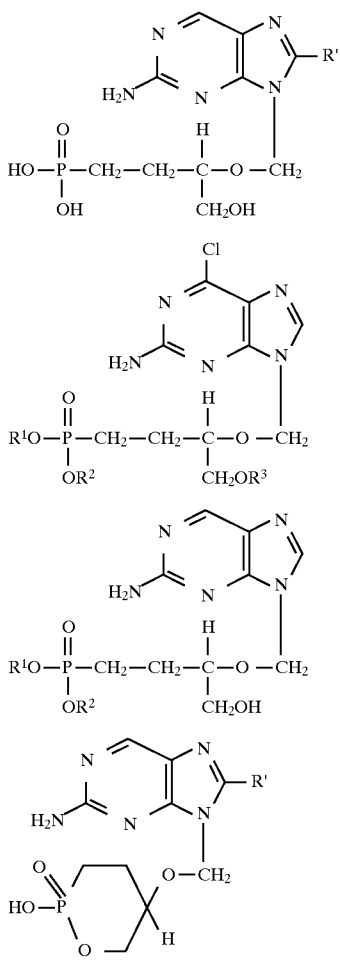

and the pharmaceutically acceptable salts and esters of these compounds. In the above formulae, $R^1$, $R^2$, $R^3$ and R' are as defined above for structure (A).

In another aspect of the invention, a pharmaceutical composition is provided for treating an individual infected with a herpes virus, the composition comprising an effective antiviral amount of an enantiomerically pure compound as provided herein or a pharmaceutically acceptable salt or ester thereof.

In another aspect of the invention, a method is provided for treating an individual infected with a herpes virus, comprising administering to the individual an effective antiviral amount of a compound as provided herein, or a pharmaceutically acceptable salt or ester thereof.

In still another aspect, the invention relates to a chiral synthesis for preparing the compounds in enantiomerically pure form.

DETAILED DESCRIPTION OF THE INVENTION

Definitions and nomenclature

Before the present compounds, compositions and methods are disclosed and described, it is to be understood that this invention is not limited to specific reagents or reaction conditions, specific pharmaceutical carriers, or to particular administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an antiviral agent" includes mixtures of antiviral agents, reference to "a pharmaceutical carrier" includes mixtures of two or more pharmaceutical carriers, and the like.

By the term "enantiomerically pure" as used herein is intended a composition containing at least about 90 wt. %, preferably at least 95 wt. %, most preferably at least 99 wt. %, of a single enantiomer.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of one to six carbon atoms, preferably one to four carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, preferably one to four, carbon atoms.

The term "acyl" is used in its conventional sense to refer to a substituent RCO— wherein R is alkyl as defined above. The term "lower acyl" refers to an acyl group wherein R contains one to six, preferably one to four, carbon atoms.

The term "halogen" to refer to a possible substituent at the 8-position of the 2-aminopurine structure is used in its conventional sense to refer to a chloro, bromo, fluoro or iodo substituent, and is typically chloro or bromo.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

By the phrase "herpes viral infection" is meant infection with any one of the known herpes viruses, i.e., herpes simplex types I or II, cytomegalovirus, herpes zoster, Epstein-Barr virus, herpes VI, herpes VII, or KSHV.

By the term "effective amount" of an antiviral agent is meant a nontoxic but sufficient amount of the agent to provide the desired treatment of the viral infection. As will be pointed out below, the exact amount required will vary from subject to subject, depending on the species, age, and general condition of the subject, the severity of the infection, the particular antiviral agent and its mode of administration, and the like. Thus, it is not possible to specify an exact "effective amount." However, a suitable "effective amount" in any particular instance can readily be determined by one of ordinary skill in the art.

By "pharmaceutically acceptable" is meant a material which is not biologically or otherwise undesirable, i.e., the material may be administered to an infected individual along with the selected antiviral agent without causing any undesirable biological effects or interacting in a deleterious manner with any of the other components of the pharmaceutical composition in which it is contained.

The Antiviral Agents

The 2-aminopurine moieties with which the present invention is concerned are purine moieties which have a nucleus of the formula

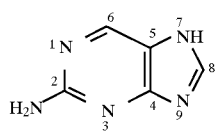

which has the numbering system shown. In the present compounds, the acyclic or cyclic phosphonate moiety is bound to the 2-aminopurine nucleus at position 9; further substitutions can be made at position 8, as indicated by the moiety R' in the structural formulae herein.

The novel compounds are represented by structural formula (A), with preferred compounds represented by structural formulae (I), (IV), (V) and (VI) as shown above, wherein $R^1$ and $R^2$ are independently selected from the group consisting of hydrogen and lower alkyl, $R^3$ is lower alkyl or —$(CH_2)_n$—$C_6H_5$, n is an integer in the range of 0 to 6 inclusive, R' is selected from the group consisting of hydrogen, hydroxyl, carboxyl, alkoxy, amino and halogen, R" is hydrogen or a halogen substituent, and wherein the compounds are in enantiomerically pure form. Thus, the invention encompasses: the isolated (S) and (R) isomers of compound (I), shown below as compounds (Ia) and (Ib), respectively; the isolated (S) and (R) isomers of compound (IV), shown below as compounds (IVa) and (IVb), respectively; the isolated (S) and (R) isomers of compound (V), shown below as compounds (Va) and (Vb), respectively; and the isolated (S) and (R) isomers of compound (VI), shown below as compounds (VIa) and (VIb), respectively.

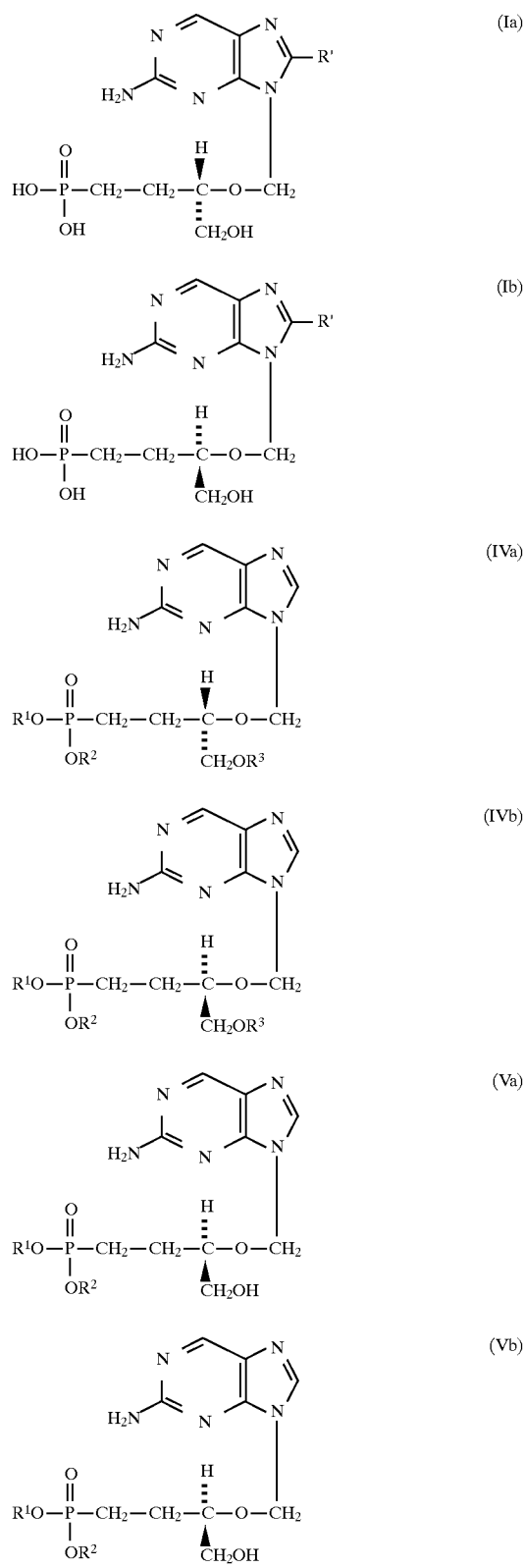

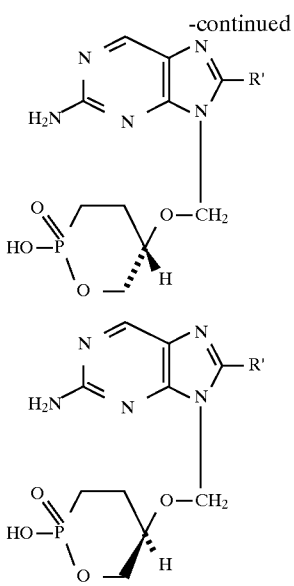

As used herein, because the compounds of the invention are in enantiomerically pure form, the designation of a compound as having the structure of formula (I) means that the compound has either structure (Ia) or (Ib), the designation of a compound as having the structure of formula (IV) means that the compound has either structure (IVa) or (IVb), etc.

The compounds may be in the form of pharmaceutically acceptable salts or esters.

Salts of the compounds can be prepared using standard procedures known to those skilled in the art of synthetic organic chemistry and described, for example, by J. March, *Advanced Organic Chemistry: Reactions Mechanisms and Structure*, 4th Ed. (New York: Wiley-Interscience, 1992). Acid addition salts are prepared from the free base (i.e., having a neutral —NH$_2$ group at the 2-position) using conventional means, involving reaction with a suitable acid. Typically, the base form of the compound is dissolved in a polar organic solvent such as methanol or ethanol and the acid is added at a temperature of about 0° C. to about 100° C., preferably at ambient temperature. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base.

Preparation of basic salts of acid moieties which may be present (e.g., a carboxylic acid group at the 8-position) are prepared in a similar manner using a pharmaceutically acceptable base such as sodium hydroxide, potassium hydroxide, ammonium hydroxide, calcium hydroxide, trimethylamine, or the like.

Preferred pharmaceutically acceptable salts of the novel compounds are phosphonic acid salts, wherein the free phosphonic acid moiety is converted to the mono- or dibasic salt form by treatment with an appropriate base. Phosphonic acid salts are prepared by treating the corresponding free acids with at least one or at least two molar equivalents of a pharmaceutically acceptable base as set forth above. The reaction is conducted in water, alone or in combination with an inert, water-miscible organic solvent at a temperature of about 0° C. to about 100° C., preferably at ambient temperature. Typical inert, water-miscible organic solvents include methanol, ethanol and dioxane. The stoichiometry of the resulting salt is dependent on the stoichiometry of the reaction components. The phosphonic acid salts can be reconverted to the phosphonic acid by standard procedures, e.g., by neutralization with an acidic resin or, less preferably, with an organic acid.

Preparation of esters involves functionalization of hydroxyl and/or carboxyl groups which may be present. These esters are typically acyl-substituted derivatives of free alcohol groups, i.e., moieties which are derived from carboxylic acids of the formula RCOOH where R is alkyl, and preferably is lower alkyl. Preferred pharmaceutically acceptable esters are phosphonic acid esters which are prepared by transesterification using methods known to those skilled in the art and/or described in the pertinent literature. See, e.g., Jones and Moffatt, *J. Am. Chem. Soc.* 90:5337 (1968). Phosphonic acid esters are encompassed by formulae (A), (IV) and (V) herein when the substituents $R^1$ and $R^2$ are other than hydrogen, i.e., are lower alkyl. Phosphonic acid esters can be reconverted to the free acids, if desired, by using conventional hydrogenolysis or hydrolysis procedures.

Pharmaceutical Compositions and Treatment Methods

The compounds of the invention defined by structural formula (A), and particularly those encompassed by formulae (Ia), (Ib), (VIa) and (VIb), including the pharmaceutically acceptable salts and esters thereof, have antiviral activity against one or more herpes viral infections. In addition, the novel synthetic intermediates represented by structural formulae (IVa), (IVb), (Va), and (Vb) are also useful as antiviral prodrugs, and may accordingly be administered to treat herpes viral infections as well. The invention thus encompasses novel pharmaceutical compositions containing an antiviral agent having the structural formula (A), and any individual compounds encompassed by formulae (Ia), (Ib), (IVa), (IVb), (Va), (Vb), (VIa) or (VIb).

The novel antiviral agents may be conveniently formulated into pharmaceutical compositions composed of one or more of the compounds in association with a pharmaceutically acceptable carrier. *Remington: The Science and Practice of Pharmacy,* 19th Ed. (Easton, Pa.: Mack Publishing Co., 1995), discloses typical methods of preparation known in the art.

The compounds may be administered orally, topically, buccally, vaginally, parenterally, or the like, depending on the nature of the herpes viral infection being treated. The term "parenteral" as used herein is intended to include subcutaneous, intravenous, and intramuscular injection.

For internal infections the compositions are preferably administered orally or parenterally at dose levels of about 0.1 to 300 mg/kg, preferably 1.0 to 30 mg/kg of mammal body weight and can be used in humans in a unit dosage form administered one to four times daily in the amount of 1 to 250 mg per unit dose.

For oral administration, the composition will generally take the form of a tablet or capsule, or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the antiviral agent is combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

For treatment of topical infections, e.g., infections around the mouth or on the skin, the compositions are applied to the infected part of the body of the patient in a topical pharmaceutical composition containing a suitable carrier. The carrier is one which is generally suited to topical drug administration and includes any such materials known in the art. The topical carrier is selected so as to provide the composition in the desired form, e.g., as a liquid, lotion, cream, paste, gel, powder, or ointment, and may be comprised of a material of either naturally occurring or synthetic origin. It is essential, clearly, that the carrier not adversely affect the active agent or other components of the pharmaceutical composition. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Particularly preferred formulations herein are colorless, odorless ointments, lotions and creams.

Ointments are semisolid preparations which are typically based on petrolatum or other petroleum derivatives. The specific ointment base to be used, as will be appreciated by those skilled in the art, is one that will provide for optimum drug delivery. As with other carriers or vehicles, an ointment base should be inert, stable, nonirritating and nonsensitizing. As explained in *Remington: The Science and Practice of Pharmacy,* supra, at pages 1399–1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be had to *Remington: The Science and Practice of Pharmacy* for further information.

Lotions are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Creams containing the selected antiviral agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant.

The present pharmaceutical compositions may also be in the form of a sterile injectable preparation, for example a sterile injectable aqueous or oleaginous suspension. This suspension may be formulated according to techniques known in the art using suitable dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium.

Preferred formulations for vaginal drug delivery are ointments and creams, as described above. Also preferred are vaginal suppositories. Suppositories may be formulated using conventional means, e.g., compaction, compression-molding or the like, and will contain carriers suited to vaginal drug delivery, typically a bioerodible material which provides for the desired drug release profile.

Formulations for buccal administration include tablets, lozenges, gels and the like. Alternatively, buccal administration can be effected using a transmucosal delivery system such as the controlled release system marketed by ALZA Corporation (Palo Alto, Calif.) under the tradename OROS®.

Viral infections of the eye, such as herpetic keratitis, may be treated by use of a sustained release ophthalmic drug delivery system as is known in the art. For ophthalmic use, the compounds can be formulated as micronized suspensions in isotonic, pH adjusted sterile saline, or preferably, as solutions in isotonic, pH adjusted sterile saline, either with or without a preservative such as benzalkonium chloride. Alternatively, for ophthalmic use, the active agent may be formulated in an ointment as described above.

The concentration of antiviral agent in any of the above formulations is generally in the range of approximately 0.01 to 15%, preferably 0.1 to 10%, and more preferably 0.1 to about 5%.

The pharmaceutical compositions of the invention may contain more than one antiviral agent as provided herein. Additional, known antiviral agents or other therapeutic compounds may be incorporated into the compositions as well.

The regimen for administration of the compounds and compositions disclosed herein will necessarily be dependent upon the needs of the individual subject being treated, the type of treatment and the judgment of the attending practitioner. Generally, the dosage regimen will follow that used in conjunction with the administration of known antiviral agents useful for treating herpes infections, e.g., acyclovir, famciclovir, foscarnet, ganciclovir, idoxuridine, sorivudine, trifluridine, valacyclovir, vidarabine, and the like.

Synthetic Methods

The invention further includes a chiral synthesis is provided for preparing the antiviral agents of the invention in enantiomerically pure form.

The synthesis involves providing as a starting material an enantiomerically pure hydroxy-containing phosphonate compound having the structural formula

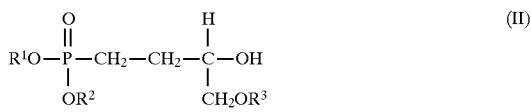

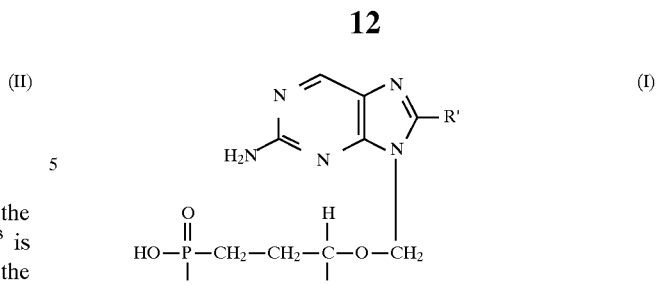

wherein R' is hydrogen.

The compound of formula (I) may be modified at the 8-position to provide other, non-hydrogen R' substituents, using procedures which can be carried out at any time during the above synthesis, and, may, as will be appreciated by those skilled in the art, be done using standard chemical techniques. Typically, modification at the 8-position will involve bromination followed by displacement of the 8-bromo functionality with an azide, thiol, or the like.

As the aforementioned procedure may be used in such a way that chirality of the starting material is maintained, the synthesis may be used to provide the (S)-isomer of compound (I), compound (Ia), using (IIa) as the starting material

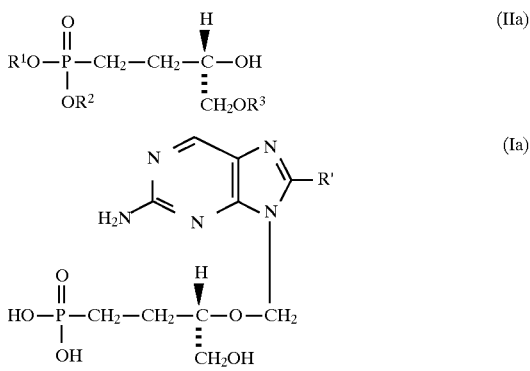

wherein $R^1$ and $R^2$ are independently selected from the group consisting of hydrogen and lower alkyl, and $R^3$ is lower alkyl or —$(CH_2)_n$—$C_6H_5$ where n is an integer in the range of 0 to 6 inclusive. The 3-hydroxy group of this starting material is then converted to a 3-chloromethyl ether substituent using suitable reagents and reaction conditions; for example, the starting compound may be treated with gaseous HCl and paraformaldehyde at a temperature below about 0° C., preferably at a temperatures approximating −10° C. The 3-chloromethyl ether phosphonate (III) is thus provided:

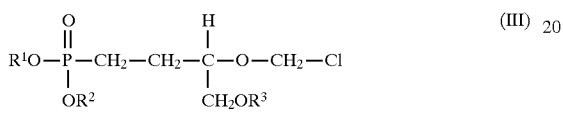

In the next step of the synthesis, the 3-chloromethyl ether phosphonate intermediate, compound (III), is conjugated to the purine moiety, as follows. 2-amino-6-chloropurine and compound (III) are admixed in the presence of a strong base, e.g., sodium hydride, in an organic solvent. Optimally, the reaction is allowed to proceed for at least about one hour, at which point the 9-substituted 2-amino-6-chloropurine (IV) may be isolated from the admixture:

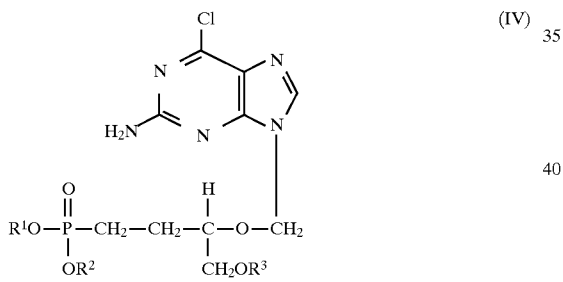

Compound (IV) is then deprotected at $R^3$ and the 6-chloro functionality removed by refluxing compound (IV) with a hydride donor, e.g., ammonium formate, and a deprotecting agent for $R^3$. When $R^3$ is benzyl, 10% palladium/carbon is an exemplary deprotecting agent. Reaction is allowed to proceed for at least about two hours to yield compound (V):

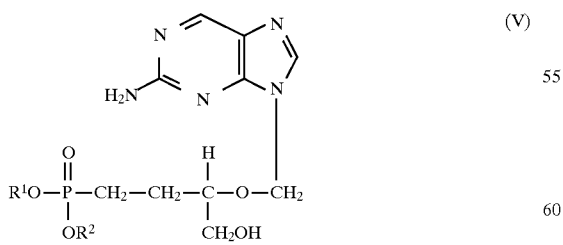

If $R^1$ and $R^2$ are other than hydrogen, i.e., if compound (V) is a phosphonic acid mono- or diester, compound (V) is converted to a phosphonate by treatment with a suitable reagent, e.g., bromotrimethylsilane. Such treatment provides the phosphonate (I):

or to provide the (R)-isomer of compound (I), compound (Ib), using (IIb) as the starting material

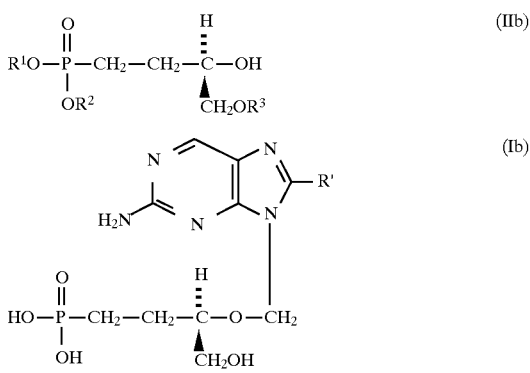

Cyclic compounds (VIa) and (VIb) may then be synthesized directly from compounds (Ia) and (Ib), respectively, via a formal dehydration reaction in the presence of a dehydrating agent such as dicyclohexylcarbodiimide.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent documents, journal articles and other references cited herein are incorporated by reference in their entireties.

EXPERIMENTAL

The following examples are put forth so as to provide those of ordinary skill in the art with a complete disclosure and description of how to carry out the synthetic methods of the invention and make the enantiomerically pure antiviral agents claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

Example 1 describes preparation of 2-amino-9-[CR(−)-1-hydroxymethyl-3-diethylphosphono)-1-propyloxymethyl]-9H-purine 1-5 as shown in Scheme 1. Briefly, the synthesis set forth in Scheme 1 involves, regiospecifically opening 2-(benzyloxymethyl) oxirane 1-1 with lithiated diethyl methylphosphonate in the presence of boron trifluoride etherate to afford 1-2 in 94% yield (Example 1, section (a.)). Compound 1-2 was then transformed to the corresponding chloromethyl ether and condensed with 2-amino-6-chloropurine in the presence of sodium hydride to give the nucleoside phosphonate 1-3 in 53% yield (Example 1, section (b.)). Treatment of 1-3 with 10% palladium/carbon and ammonium formate gave the 2-aminopurine phosphonate 1-4 in 66% yield (Example 1, section (c)). Finally, compound 1-4 was treated with excess bromotrimethylsilane to give the desired nucleoside phosphonate 1-5 in 35% yield (Example 1, section (d.)). Optical purity of compounds was determined by HPLC using a chiral column.

Example 2 describes preparation of the corresponding (S)-isomer, using the route shown in Scheme 2. Examples 3 and 4 describe preparation of cyclic analogs. Antiviral activity was evaluated as described in Example 5.

Scheme 1

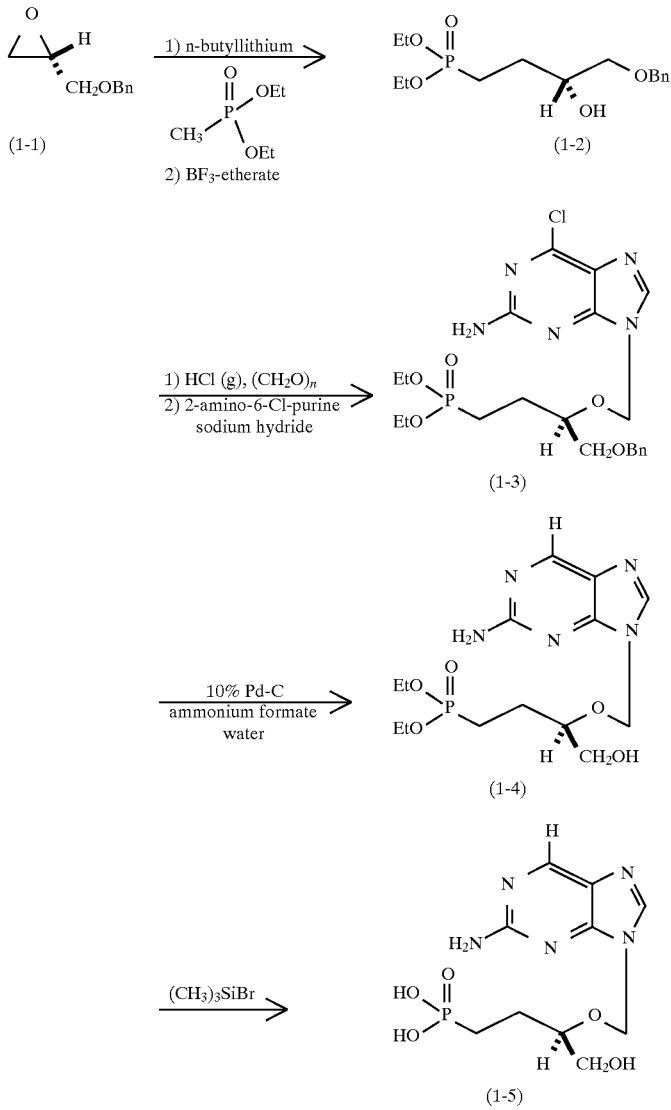

-continued
Scheme 1
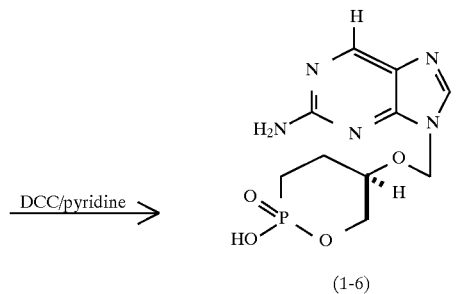
(1-6)
Scheme 2
Scheme 2: (S)-enantiomer
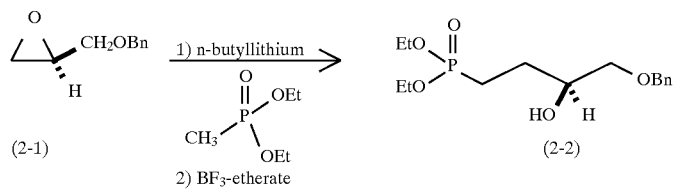
(2-1)  (2-2)
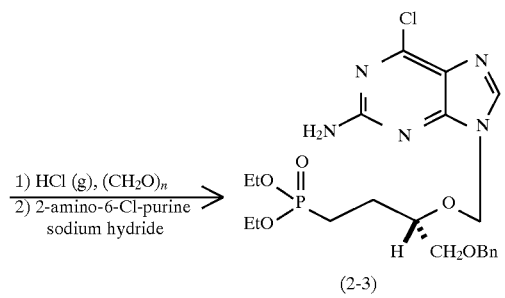
(2-3)
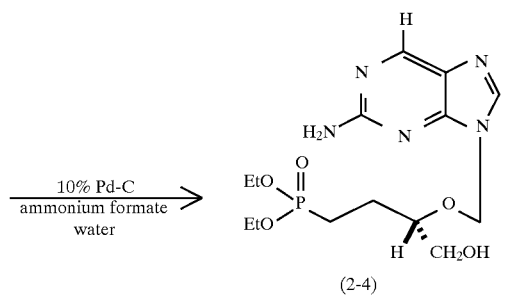
(2-4)
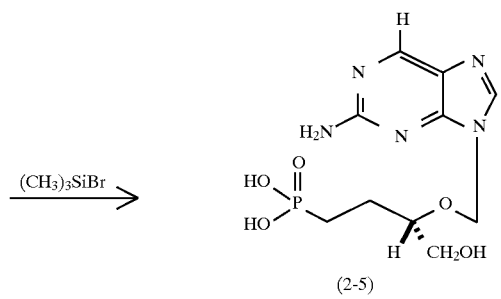
(2-5)

-continued
Scheme 2

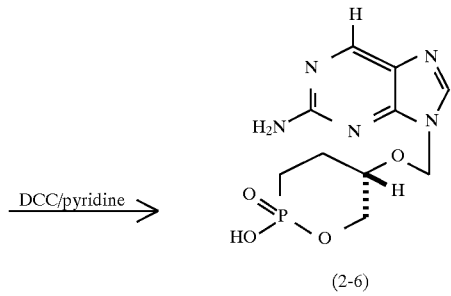

(2-6)

EXAMPLE 1

Synthesis of 2-Amino-6-Hydroxyethylthio-9-[(R(−)-1-Hydroxymethyl-3-Diethylphosphono)-1-Propyloxymethyl]-9H-Purine (1-5)

(a.) Preparation of (R)-(+)-diethyl-4-O-benzyl-3,4-dihydroxybutylphosphonate (1-2):

A solution of n-butyllithium (2.5M in hexane, 72 mL, 180 mmol) was added dropwise to a solution of diethyl methylphosphonate (27.4 g, 180 mmol) in 200 mL dry tetrahydrofuran (THF) at −78° C. After 30 minutes of stirring at −78° C., the resulting white suspension was added in a slow stream through a cannula to a stirred solution of $BF_3.Et_2O$ (22.13 mL, 180 mmol) in THF (400 mL) at −78° C. After 10 minutes, neat (R)-(−)-2-(benzyloxymethyl)oxirane 1-1 (10 g, 61 mmol, obtained from the Aldrich Chemical Co.) was added quickly to this suspension. The reaction mixture was stirred for 30 minutes at −78° C., quenched by adding saturated aqueous $NaHCO_3$ (100 mL) and allowed to warm to room temperature. The reaction was diluted with 450 mL of ether and washed with 2×200 mL of saturated sodium bicarbonate solution and 100 mL of brine. The ether layers were dried ($MgSO_4$) and evaporated. The residue was chromatographed on silica gel, eluting with 5% methanol/95% dichloromethane to give the product 1-2 as a pale yellow oil (18.0 g, 94%).

$R_f$=0.43 silica ($CH_2Cl_2$/MeOH: 95/5); $^1$H NMR ($CDCl_3$) δ 7.33 (m, 5H), 4.55 (s, 2H), 4.09 (m, 2H), 3.82 (m, 1H), 3.35–3.50 (m, 2H), 1.65–2.00 (m, 4H), 1.32 (t, 6H).

(b.) Preparation of 2-amino-6-chloro-9-[(R(−)-1-benzyloxymethyl-3-diethylphosphono)-1-propyloxymethyl]-9H-purine (1-3)

A suspension of 1-2 (12.6 g, 39.8 mmol) and paraformaldehyde (3.5 g) in dry 1,2-dichloroethane (250 mL) was treated for 2 hr at −10° C. with gaseous HCl, by which time all of the paraformaldehyde had dissolved. NMR analysis indicated complete conversion to the chloromethyl ether. Argon was then bubbled through the resulting clear solution for 40 min at room temperature to remove excess HCl. The solution was dried over $CaCl_2$, evaporated to dryness and dissolved in dry dimethylformamide (70 mL).

A solution of the sodium salt of 2-amino-6-chloro purine, prepared from 2-amino-6-chloropurine (8.94 g, 52.7 mmol) and NaH (2.24 g, 60% in oil, 56 mmol) in 90 mL of DMF (stirred at room temperature for 1 hour) was cooled to −50° C. and the DMF solution of the chloromethyl ether was added. The bath temperature was raised to −20° C. and after 1 hr of stirring at −20° C., the reaction mixture was poured into dichloromethane (350 mL) and washed with saturated aqueous $NaHCO_3$. The aqueous layer was extracted three times with three 200 mL portions of dichloromethane, the organic extract washed with brine, dried ($Na_2SO_4$) and evaporated to dryness. The crude product was purified by silica gel chromatography using dichloromethane/methanol (97.5/2.5) to give 10.4 g of the product 1-3 as a pure colorless thick oil.

$R_f$=0.55 silica ($CH_2Cl_2$/MeOH: 95/5); $^1$H NMR ($CDCl_3$) δ 7.88 (s, 1H), 7.32 (m, 5H), 5.62 (s, 2H), 5.40 (s, 2H), 4.51 (s, 2H), 3.95–4.15 (m, 4H), 3.85 (m, 1H), 3.47 (d, J=4.9 Hz, 2H), 1.60–1.90 (m, 4H), 1.25–1.35 (t, J=7 Hz, 6H).

After removal of 1-3, continued elution of the column gave 25% of the 7-substituted isomer, $R_f$=0.33 silica ($CH_2Cl_2$/MeOH, 95/5).

(c.) Preparation of 2-amino-9-[(R(−)-1-hydroxymethyl-3-diethylphosphono)-1-propyloxymethyl]-9H-purine (1-4)

A mixture of 1-3 (14.0 g, 28.1 mmol), ammonium formate (12.6 mg in 350 mL methanol, 0.57M), 10% palladium/carbon (10 g), and water (250 mL) was refluxed for 3 hours. The reaction mixture was then filtered through Celite® (Sigma Chemical Company) and the solvents evaporated to dryness in vacuo to give 8.83 g (85%) of the product 1-4 as a cloudy oil.

$R_f$=0.28 silica ($CH_2Cl_2$/MeOH: 90/10); $^1$H NMR ($CD_3OD$) δ 8.58 (s, 1H), 8.21 (s, 1H), 5.67 (s, 2H), 3.98 (m, 4H), 3.74 (m, 1H), 3.55 (m, 2H). 1.60 (m, 4H), 1.26 (m, 6H). The compound was used without purification in the next step.

(d.) 2-Amino-9-[(R(−)-1-hydroxymethyl-3-phosphono)-1-propyloxymethyl]-9H-purine (1-5)

A solution of 1-4 (6.88 g, 18.4 mmol) in a mixture of dichloromethane (150 mL) and hexamethyldisilazane (150 mL) was treated with fresh, colorless bromotrimethylsilane (24.0 mL, 181 mmol) overnight at room temperature. The solvents were removed, and the residue was dissolved in 50% ethanol-water (50 mL). The solvents were evaporated to dryness to give crude 1-5 as a white powder (7.5 g). The solid was chromatographed on a reverse phase column (Bakerbond Octadecyl $C_{18}$) eluting with water. Evaporation of the eluant and drying under high vacuum at 100° C. gave 2.05 g (35%) of pure product 1-5.

$R_f$=0.15 silica ($CH_3CN$/0.1N $NH_4Cl$, 7:3); UV ($H_2O$) $\lambda_{max}$ 242.9 nm (ε5823), 304.1 (6529); $[\alpha]_D^{21}$=−9.31 (c=1.085, $H_2O$); $^1$H NMR ($D_2O$) δ 8.64 (s, 1H), 8.40 (s, 1H), 5.65 (s, 2H), 3.60 (m, 2H), 3.47 (m, 1H), 1.64 (m, 2H), 1.39 (m, 2H); Calcd. for $C_{10}H_{16}N_5O_5P$: C, 36.26; H, 4.95. Found: C, 36.64; H, 5.26.

EXAMPLE 2

The procedure of Example 1 may be used to carry out the synthesis illustrated in Scheme 2, to prepare the corresponding (S)-isomer, compound 2-5, using the (S)-isomer of the 2-(benzyloxymethyl)oxirane starting material, i.e., compound 2-1.

EXAMPLE 3

Synthesis of 2-Amino-9-[(R(+)-1-Hydroxymethyl-3-Phosphono-1-Propyloxymethyl]-9H-Purine, Cyclic Ester (1-6)

A sample of 1-5 (2-amino-6-hydroxyethylthio-9-[(R(-)-1-hydroxymethyl-3-diethylphosphono)-1-propyloxymethyl]-9H-purine (0.5 g, 1.58 mmol) was dissolved in 10 mL of water and 40 mL of pyridine. Dicyclohexylcarbodiimide (1.30 g, 6.3 mmol) was added and the reaction was stirred at room temperature for 48 hr and evaporated to dryness in vacuo. The residue was treated with 50 mL of water and filtered. The aqueous filtrate was evaporated. The resulting solid was triturated with 10 mL of absolute ethanol. The triturated solid was dried under high vacuum at 100° C. to give 392 mg (83%) of pure product 1-6.

$R_f$=0.30 silica (CH$_3$CN/0.1N NH$_4$Cl, 7:3); UV (H$_2$O) $\lambda_{max}$ 243.3 nm ($\epsilon$5839), 304.1 (6329); $[\alpha]_D^{21}$=+8.20 (c=1.00, H$_2$O); $^1$H NMR (D$_2$O) δ 8.63 (s, 1H) 8.41 (s, 1H), 5.62 (s, 2H), 4.09 (m, 2H), 3.78 (m, 1H), 2.13 (m, 2H), 1.62 (m, 2H). Calcd. for C$_{10}$H$_{14}$N$_5$O$_4$P: C, 40.14; H, 4.72; N, 23.40. Found: C, 40.27; H, 4.91; N, 23.00.

EXAMPLE 4

The procedure of Example 3 may be used to carry out the synthesis illustrated in Scheme 2, to prepare the corresponding (S)-isomer, compound 2-6, by starting with compound 2-5 instead of 1-5.

EXAMPLE 5

The compounds prepared in Examples 1 and 3 were evaluated in vitro as antiviral agents against human cytomegalovirus.

The herpes strain employed was Strain D-16 of HCMV. Continuous passaged MRC-5 cells obtained from the American Type Culture Collection (Bethesda, Md.) were used for testing, with growth medium consisting of Minimum Essential Medium (MEM) supplemented with 0.1% NaHCO$_3$ and 50 μL gentamicin.

To a 96-well microtiter plate containing an established 24-hour monolayer of cells from which the medium had been decanted was added 0.1 mL of varying (one-half log$_{10}$) concentration of test compound, which incubated on the cell 15 minutes, after which 0.1 mL of virus in a concentration of 320 cell culture 50% infectious doses (CCID$_{50}$)/0.1 mL was added. The plate was covered with plastic wrap and incubated at 37° C. The cells were examined microscopically after 72 hours. The ED$_{50}$ (the median effective antiviral dose, i.e., that dose which is effective in 50% of the cells), CD$_{50}$ (the median cytotoxic dose, i.e., that dose which produces cytotoxicity in 50% of the cells), and TI (the therapeutic index, meaning the ratio of the median cytotoxic dose to the median effective dose) were evaluated. Results are set forth in the tables which follow.

TABLE 1

Antiviral Activity (Plaque Reduction) of 1-6 or DHPG* vs. HCMV, Strain D-16 in MRC-5 Cells (Reference SN/CHC 338-340)

| Compound concentration (μg/mL) | Cpd. 1-6 | | DHPG | |
|---|---|---|---|---|
| | Number of Plaques | % Reduction | Number of Plaques | % Reduction |
| 1000 | toxic | toxic | | |
| 316 | 0.0 | 100 | 0.0 | 100 |
| 100 | 0.0 | 100 | 0.0 | 100 |
| 32 | 6.5 | 92 | 2.0 | 98 |
| 10 | 33.0 | 59 | 24.5 | 70 |
| 3.2 | 56.0 | 31 | 57.0 | 0 |
| 1 | 51.0 | 37 | 69.0 | 0 |
| 0.32 | | | | |
| 0.1 | | | | |
| ED$_{50}$ (μg/mL): | 6.7 | | 7.2 | |
| CD$_{50}$ (μg/mL): | 487 | | >316 | |
| TI: | 73 | | >44 | |

*9-[(1,3-dihydroxy-2-propoxy)methyl] guanine

TABLE 2

Activities of 1-5 and 1-6 Against a murine cytomegalovirus infection in normal BALB/c mice.

| Compound | Dose$^a$ (mg/kg/day) | Survivors/Total (%) | Mean Day to Death |
|---|---|---|---|
| 1-5 | 40 | 10/10 (100)*** | >21 |
| | 20 | 8/10 (80)*** | 11.5 ± 0.7* |
| | 10 | 7/10 (70)** | 10.0 ± 3.6* |
| | 5 | 5/10 (50)* | 9.6 ± 4.6* |
| Placebo | — | 2/20 (10) | 5.2 ± 0.7 |
| 1-6 | 40 | 4/10 (40)** | 8.3 ± 4.9 |
| | 20 | 3/10 (30) | 6.1 ± 0.4 |
| | 10 | 0/10 (0) | 7.4 ± 2.0 |
| | 5 | 0/10 (0) | 6.4 ± 0.5 |
| Placebo | — | 0/20 (0) | 6.4 ± 1.1 |

$^a$Treatments were given once daily for 5 days starting 24 hours after virus challenge.
*P < 0.05, P < 0.01, *P < 0.001.

TABLE 3

Toxicity of 1-5 to uninfected BALB/c mice.

| Compound | Dose$^a$ (mg/kg/day) | Survivors/Total (%) | Weight Change$^b$ | Kidney Damage (%) |
|---|---|---|---|---|
| 1-5 | 600 | 3/3 (100) | +4.5 | 0 |
| | 400 | 3/3 (100) | +6.6 | 0 |
| | 200 | 3/3 (100) | +7.8 | 0 |
| | 100 | 3/3 (100) | +7.0 | 0 |
| Placebo | — | 3/3 (100) | +8.7 | 0 |

$^a$Treatments were given once daily for 15 days.
$^b$Difference in weight (in grams) between day 0 and day 16.

We claim:
1. A compound having the structural formula (A)

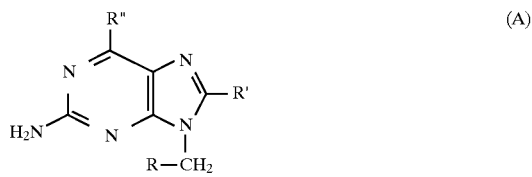

in enantiomerically pure form, wherein:

R is selected from the group consisting of:

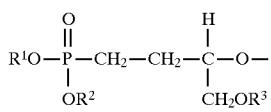

and

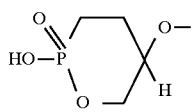

in which $R^1$ and $R^2$ are independently selected from the group consisting of hydrogen and lower alkyl, $R^3$ is lower alkyl or $-(CH_2)_n-C_6H_5$, and n is an integer in the range of 0 to 6 inclusive;

R' is selected from the group consisting of hydrogen, hydroxyl, carboxyl, alkoxy, amino and halogen; and R" is hydrogen or a halogen substituent, or a pharmaceutically acceptable salt or ester thereof.

2. The compound of claim 1, having the structural formula (Ia)

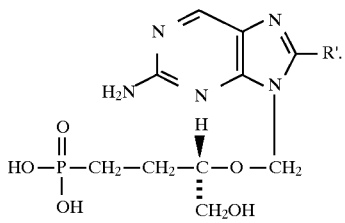

3. The compound of claim 1, having the structural formula (Ib)

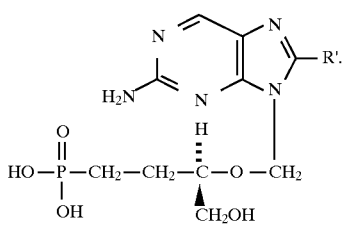

4. The compound of claim 1, having the structural formula (IVa)

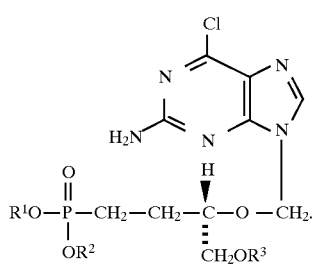

5. The compound of claim 1, having the structural formula (IVb)

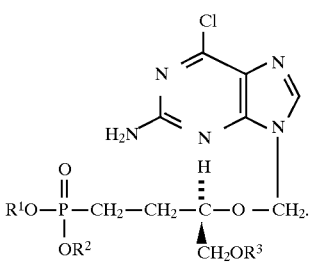

6. The compound of claim 1, having the structural formula (Va)

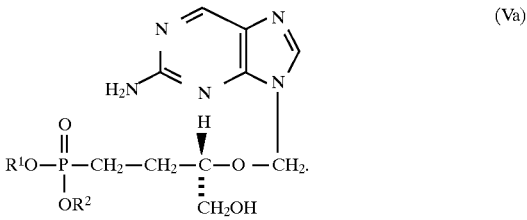

7. The compound of claim 1, having the structural formula (Vb)

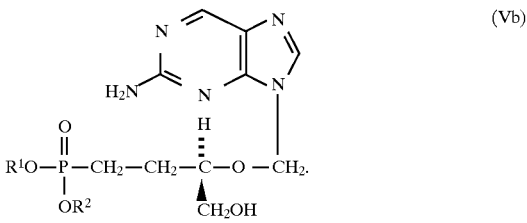

8. The compound of claim 1, having the structural formula (VIa)

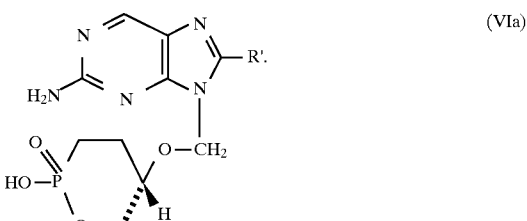

9. The compound of claim 1, having the structural formula (VIb)

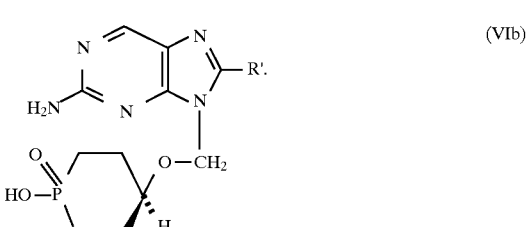

10. The compound of any one of claims 1, 2, 3, 8 or 9, wherein R' is selected from the group consisting of hydroxyl, amino, and halogen.

11. The compound of claim 10, wherein R' is hydrogen.

12. A pharmaceutical composition for treating herpes viral infection which comprises an effective amount of the compound of claim 1 in admixture with a pharmaceutically acceptable carrier.

13. The pharmaceutical composition of claim 12, comprising a formulation suitable for oral administration.

14. The pharmaceutical composition of claim 12, comprising a formulation suitable for topical administration.

15. A method to treat herpes viral infection in an infected subject, which comprises administering to the subject an effective antiviral amount of the compound of claim 1.

16. The method of claim 15, wherein the herpes viral infection is herpes zoster.

17. The method of claim 15, wherein the herpes viral infection is herpes simplex virus I.

18. The method of claim 15, wherein the herpes viral infection is herpes simplex virus II.

19. The method of claim 15, wherein the herpes viral infection is cytomegalovirus.

20. The method of claim 15, wherein the herpes viral infection is Epstein-Barr virus.

21. The method of claim 15, wherein the herpes viral infection is human herpes virus VI.

22. The method of claim 15, wherein the herpes viral infection is human herpes virus VII.

23. The method of claim 15, wherein the herpes viral infection is Kaposi's sarcoma herpes virus.

24. A compound having the structural formula (A)

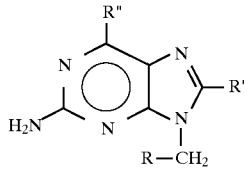 (A)

in enantiomerically pure form, wherein:

R is selected from the group consisting of

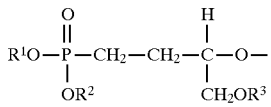

and

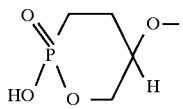

in which $R^1$ and $R^2$ are independently selected from the group consisting of hydrogen and lower alkyl, $R^3$ is lower alkyl or $-(CH_2)_n-C_6H_5$, and n is an integer in the range of 0 to 6 inclusive;

R' is selected from the group consisting of hydrogen, hydroxyl, carboxyl, alkoxy, amino and halogen; and R" is hydrogen, or a pharmaceutically acceptable salt or ester thereof.

* * * * *